United States Patent [19]
Haskell

[11] Patent Number: 6,082,996
[45] Date of Patent: Jul. 4, 2000

[54] ORAL HABIT RETRAINING DEVICE

[75] Inventor: Bruce Haskell, P.O. Box 197027, Louisville, Ky. 40259-7027

[73] Assignee: Bruce Haskell, Louisville, Ky.

[21] Appl. No.: 09/310,020

[22] Filed: May 11, 1999

[51] Int. Cl.[7] .................................................. A61C 3/00
[52] U.S. Cl. ............................................................ 433/18
[58] Field of Search .................................. 433/7, 18, 20, 433/22; 606/234, 235; 128/848, 860, 857, 859; 54/7, 8, 9; 63/38, 39; 601/38

[56] References Cited

U.S. PATENT DOCUMENTS

| | | | |
|---|---|---|---|
| 411,249 | 9/1889 | Pape ............................................. | 63/38 |
| 1,245,965 | 11/1917 | Pratt ............................................. | 63/38 |
| 4,005,564 | 2/1977 | Simington ..................................... | 54/8 |
| 4,179,815 | 12/1979 | Hoffman ................................... | 433/140 |
| 4,571,178 | 2/1986 | Rosenberg .................................... | 433/7 |
| 4,606,348 | 8/1986 | Panicci ...................................... | 606/234 |
| 4,608,974 | 9/1986 | Sicurelli, Jr. ............................. | 128/136 |
| 5,007,828 | 4/1991 | Rosenberg .................................. | 433/18 |
| 5,160,344 | 11/1992 | Werton ..................................... | 606/235 |
| 5,176,514 | 1/1993 | Viazis ......................................... | 433/2 |
| 5,779,470 | 7/1998 | Kussick ....................................... | 433/6 |

FOREIGN PATENT DOCUMENTS

| | | | |
|---|---|---|---|
| 818242 | 10/1951 | Germany ............................... | 606/235 |

OTHER PUBLICATIONS

"An aid to stop thumb sucking: the "Bluegrass" appliance", Pediatric Dentistry, Haskell, vol. 13, No. 2, pp. 83–85, Mar./Apr. 1991.
Twin Block Functional Therapy, Applications in Dentofacial Orthopaedics, Chapter 12: Treatment of Anterior Open Bite, Clark, pp. 147–148, 1995.
"The Modified Bluegrass Appliance", Baker, J.S.S.P.D., vol. 4, No. 3, pp. 20–21, 1998.
TP Orthodontics, Inc. Product Catalog, Bluegrass Roller, p. 189, 1998.

*Primary Examiner*—Todd E. Manahan
*Attorney, Agent, or Firm*—Holme Roberts & Owens LLP

[57] ABSTRACT

An improved orthodontic oral habit retraining device is disclosed. The device may comprise two identical halves, or roller sections, configured to be matingly bonded together at chair side. Once bonded, the assembled roller may define a cylindrical shape with a hollow axial opening therethrough. In one arrangement, the exterior surface of the roller is hexagonal in cross-section. During the step of bonding the two halves together, the halves are positioned about any of a number of known, standard, wire form-type orthodontic appliances. Upon bonding, the device is free to spin or roll about the wire and to move laterally on the wire structure of the orthodontic appliance. Installation typically results in positioning of the roller forward in the vault of the palate of a patient, directly adjacent the tip of the patient's tongue.

41 Claims, 8 Drawing Sheets

ORAL HABIT RETRAINING DEVICE

FIELD OF THE INVENTION

The present invention relates to the field of orthodontics, and more particularly, to an improved oral habit retraining device that may be readily installed on a wire member of an orthodontic device positionable in the vault of the palate of a patient.

BACKGROUND OF THE INVENTION

The deleterious effects of the oral habits of thumb sucking and tongue thrusting are well recognized. Such habits develop at birth and are believed to be broadly related to the instinctive sucking reflex associated with breast feeding. Although such habits typically fade after the first year of life, in many cases they do not, and for complex psychological reasons such habits become ingrained as the effected individuals increase in age.

Thumb sucking, or digit sucking, if continued after the first year of life causes a constriction of both the mandibular and maxillary arches, a narrowing of the palate, and a number of other adverse skeletal effects. In severe cases where an adolescent demonstrates the habit, the resulting sequela can involve all of the bony structures below the floor of the cranium. Such results can dramatically affect facial profile with severe skeletal and of course severe orthodontic consequences. This can detract from not only physical appearance but can also cause holistic problems which affect the overall health of an individual. By way of example, such habits can result in or exacerbate airway problems.

As a further example of problems that can result from digit sucking, consider a young toddler with dental arches that have been narrowed due to the habit. The child may then develop a lateral preference to the left or right simply so that he or she can conveniently chew food. This is the classic scenario for the onset of an anterior cross-bite.

As noted, tongue thrusting is another destructive oral habit. It involves an abnormal swallowing sequence. In this regard, it should be appreciated that normal swallowing involves a complex, coordinated cycle of muscle reflexes at the back of the throat, the lower face and the tongue. A person exhibiting a tongue thrusting habit will include a non-necessary additional movement where the tongue is pushed upward toward the front of the palate and forcibly forward against the lingual surface of the anterior teeth. Over time, this destructive habit can cause dramatic flaring of the front teeth accompanied by major diastemas between the teeth. Like thumb sucking, a narrowing of the arch and other abnormal physiology can result. This condition, when combined with a molar Class II retrognathic mandible poses one of the most severe orthodontic conditions encountered by orthodontists.

Two distinct approaches have been proposed for attempting to address the above-noted destructive oral habits. In a first approach, orthodontic appliances are utilized which can be positioned within a mouth to engage the digit or the tongue when the oral habit activity is attempted. Such appliances are of a static nature and may assume a "hay rake" configuration to yield painful feedback upon contact. In the later regard, this kind of negative reinforcement approach has proven to be of questionable efficacy and may result in other problems for a patient.

In a second more recent approach, orthodontic habit retraining devices having a palatally positioned roller have been utilized. The palatally positioned roller provides positive sensory feedback when contacted by the tip of the patient's tongue. One such device known as the "Bluegrass" appliance has been developed by the present inventor to yield positive results. See, Haskell, "An aid to stop thumb sucking: The Bluegrass appliance" Pediatric Dentistry, March/April, 1991 at 83–85. To date, however, devices of this nature have not been widely employed. In this regard, it is noted that the use of such devices has been limited to implementations in which a roller is mounted on a dedicated orthodontic device at the time of fabrication of the device.

SUMMARY OF THE INVENTION

In view of the foregoing, a primary objective of the present invention is to provide an oral habit retraining device which can be readily implemented on an orthodontic device, and which is otherwise designed to provide positive sensory feedback to encourage positive patient response. A related objective of the present invention is to provide an improved oral habit retraining device that can be readily implemented on various orthodontic devices post-fabrication of such appliances. Yet a further related object of the present invention is to provide an improved oral habit retraining device that can be installed on orthodontic wire appliances after installation of such appliances in a patient's mouth.

An additional objective of the present invention is to provide an oral habit retraining device that can be readily implemented on orthodontic devices to yield dual functionality.

A further object of the present invention is to provide a device having enhanced functionality via the provision of roller enhancing features that generate increased sensory response.

One or more of the above objectives and additional advantages are realized via the retraining device of the present invention which provides for the selective and convenient positioning of an inventive roller onto a wire member comprising an orthodontic device. In this regard, orthodontic appliances usable with the present invention will most typically include a wire member having a central section located between two opposing, curved sections, wherein upon direct receipt of the roller on the central section of the wire member the roller will be positionable in the vault of the palate of a patient. As will be appreciated, positioning of the roller in accordance with the present invention may be accomplished without a need for sliding the roller over either of the opposing curved sections of the wire member comprising an orthodontic appliance. As such, the present invention may be readily implemented on an orthodontic appliance after fabrication of the appliance, including implementation at chair side or after appliance installation by a practitioner.

In one aspect of the present invention, the inventive oral habit retraining device comprises separate first and second roller sections which are selectively interconnectable in opposing face-to-face relation to define a roller having a channel defined between the first and second roller sections. The roller is adapted to selectively receive the wire member of an orthodontic appliance through the roller channel upon interconnection of the first and second roller sections. The channel is sized to allow the roller to readily rotate or spin about the wire member after installation in a patient's mouth.

To enhance relative positioning and interconnection of the first and second roller sections, the first roller section may include at least one convex interface surface and the second roller section may include at least one concave interface surface, wherein the convex and concave interface surfaces are correspondingly shaped so that said concave interface surface conformally receives the convex interface surface upon interconnection of the first and second roller sections. In this regard, the first roller section and second roller section may each further include a concave interface surface and convex interface surface, respectively, wherein the concave interface surfaces of the first and second roller sections receive the convex interface surfaces of the second and first roller sections, respectively.

In one arrangement, interface surface regions of the first and second roller sections may each comprise first and second interface surfaces located on opposing sides of a groove defined across each interface surface. In this regard, the grooves of the first and second roller sections may be oriented and sized to combinatively define the wire-receiving roller channel upon interconnection of the first and second roller sections. The first and second interface surfaces on the first and second roller sections may be complimentary-shaped so that said first and second roller sections are of an identical configuration, but are positioned in reverse orientation upon interconnection. That is, the first interface surface of the first roller section may be configured to conformally interface with the second interface surface of the second roller section upon interconnection, and the second interface surface of the first roller section may be configured to conformally interface with the first interface surface of the first roller section upon interconnection.

More particularly, and in one embodiment, each of the first interface surfaces of the first and second roller sections may comprise first and second facets which adjoin to define an open angle σ therebetween of less than 180°, and preferably at an open angle σ of between 90° and 180°. Correspondingly, the second interface surfaces of the first and second roller sections each comprise first and second facets that adjoin to define an open angle β therebetween of greater than 180°, most preferably at an open angle β between 180° and 270°, wherein the angles σ and β are complimentary (i.e. wherein σ+β=360°). As such, upon interconnection of the first and second roller sections, the first interface surface of the first roller section will conformally receive the second interface surface of the second roller section and the first interface surface of the second roller section will conformally receive the second interface surface of the first roller section.

The outer surfaces of each of the roller sections may be contoured to enhance tactile interface with the tip of the tongue of a patient. In this regard, the outer surfaces may be provided so that, upon interconnection of the first and second roller sections, a roller having an elongated, e.g. cylindrical, configuration is defined. Such roller may have an outer surface of a hexagonal configuration in cross-section, wherein two of the six outer surfaces are defined by each of the first and second roller sections, and wherein the other two outer surfaces are combinatively defined by surface regions of both the first and second roller sections. As further examples, the roller may have an outer surface of a pentagonal, heptagonal, or octagonal configuration in cross-section. As will be appreciated, a number of outer surface configurations are possible, including cylindrical rollers having one or more of the following tactile elements provided thereupon: troughs, ribs, annular rings, pockets and bumps.

In yet another aspect of the present invention, the first and second roller sections may include registration surfaces that are engageable upon interconnection of the sections to establish a lateral position of the sections relative to one another. In this regard, the lateral registration surfaces may comprise a pair of opposing surfaces that restrain relative movement of the roller sections in at least one dimension when the registration surfaces are engaged. The registration surfaces may be configured for establishing a predetermined relative lateral position of the first and second roller sections such as, for example, a lateral position wherein the ends of the first and second roller sections are substantially aligned with one another. The registration surfaces may also, for example, be configured for establishing a predetermined relative position of the roller sections wherein outer surfaces combinatively defined by surface regions of both the first and second roller sections are substantially continuous and smooth.

The first and second roller sections may be comprised of a material that facilitates ready interconnection. By way of primary example, the roller sections may comprise a ceramic material, plastic material, or a combination thereof. In this regard, the selection of a translucent ceramic material, plastic material, or combination thereof, may be preferred. More particularly, the translucent material may provide for the transmission of at least about 20% of incident light therethrough. As another example, the roller sections may comprise a metallic material (e.g. steel).

In one desired arrangement, each of the first and second roller sections comprise a ceramic material having a hardness of at least about 1400 on the Rockwell 45N scale ("1400 R45N"). Most preferably, the ceramic material has a hardness of about 1680 R45N. Use of such material yields a vibratory and/or auditory response upon rolling contact with the metal wire member of an orthodontic appliance. Ceramic materials that may be employed include both mono-crystalline alumina and poly-crystalline alumina. Other bio-compatible ceramic materials may also be employed, including, among others, zirconia, transformation toughened zirconia ("TTZ"), silicon carbide, and boron carbide.

In another aspect of the present invention, the oral habit retraining device may be of a length which allows for a degree of movement along the central section of the wire member of an orthodontic appliance, i.e. between curved portions thereof. More particularly, it may be preferable to provide a roller having a length with a ratio of between about 10% and 90% relative to the length of the central section of the wire member of an orthodontic appliance (i.e. as defined by the length between the curved regions of the wire member). Such a ratio facilitates lateral movement of the roller back and forth along the wire member in response contact with the tip of the tongue of a patient, thereby enhancing additional sensory feedback.

Relatedly, it may be preferable to provide an oral habit retraining device in which the difference between the minimum width of the channel and the maximum width of the central section of the wire member is at least about 0.010 inches. Such difference in the minimum width of the channel and maximum width of the central section of the wire member allows the roller to not only spin about the wire member but additionally provides for a wiggling, rattling effect upon contact with the tip of a patient's tongue. When a relatively hard material is used to fabricate the roller, such difference further provides an auditory/vibratory effect, further increasing sensory feedback to a patient's redirected tongue movements. In the event a circular channel configuration is employed with a circular wire member, the ratio between the diameter of the wire and the diameter of the channel is preferably maintained between about 1/1.1 and 1/2.5.

In another aspect of the present invention, an improved method is provided for installation of an oral habit retraining device. In this regard, a roller having first and second roller sections as described above may be readily installed by first applying an adhesive on one or more interface surfaces of at least a first roller section. By way of example, when the first and second roller sections comprise a ceramic material (e.g. poly-crystalline alumina), such adhesive may comprise a light activated urethane dimethacrylate system. Following application of the adhesive to the first roller section, the first roller section may then been positioned on one side of the central section of the wire member of an orthodontic device. Such orthodontic device may be previously fabricated, and positioning of the first roller section relative thereto may be completed either before or after installation of the orthodontic device in a patient's mouth. Once the first roller section is positioned on one side of the central section of the wire member, the second roller section may be positioned on the opposing side (e.g. top side) of the central section of the wire member. Thereafter, the first and second roller sections may be advanced to capture the central section of the wire member in a roller channel defined by the first and second roller sections. If the roller sections include registration surfaces, respective registration surfaces may be engaged with one another to establish a lateral position of the roller sections relative to one another while the sections are being advanced to capture the wire member or after advancement of the sections has been completed. For example, after the roller sections have been advanced to a position wherein the interface surfaces are in contact with one another (i.e. to a position where the roller sections cannot be advanced further towards one another), the roller sections may be moved laterally relative to one another to engage a pair of opposing surfaces that restrict such lateral movement of the roller sections thereby establishing a lateral position of the roller sections relative to one another. Upon such contact of the interface surfaces of the roller sections with one another and engagement of their registration surfaces, if any, the first and second roller sections will adhesively interconnect in rapid fashion. It should be appreciated that, in practice, one or more of that interface surfaces may not be in actual physical contact with its corresponding interface surface. Rather, corresponding interface surfaces may be separated by a thin layer of adhesive. It should be noted that the thinner the adhesive layer, the stronger the bond may be between the roller sections.

Following installation of the present invention, it has been found that the tip of the tongue of patients will quickly find the oral habit retraining device and promptly begin to manipulate the device. Such contact closes a sensory loop that is believed to provide positive feedback as a patient becomes increasingly familiar with the contact relationship. In this regard, the patient may manipulate the roller to roll about the orthodontic appliance. Additionally, in some arrangements the patient may be able to move the roller to an extent from side to side thereby enhancing the sensory experience. Additionally, where a hard roller is employed, the weight of the roller, as well as the contact between the roller and wire member of the orthodontic device, may yield a vibratory and/or auditory response to further enhance the sensory feedback. As noted, the above-noted outer surface of the roller may be provided with any number of tactile-enhancing contouring features. In alternate embodiments, it has also been contemplated that a plurality of side-by-side rollers, (e.g. each comprising first and second roller sections), may be employed wherein a patient may be challenged to separately control rolling and/or lateral movement of the rollers.

It has been found that use of the present invention may immediately serve to affect a reduction in the destructive oral habit. It has also be recognized that sustained use of the oral habit retraining device, for example continuous use through a period of up to six months, may be preferred in order to ensure that the retraining response has been effectively ingrained.

DETAILED DESCRIPTION

Figure 1:
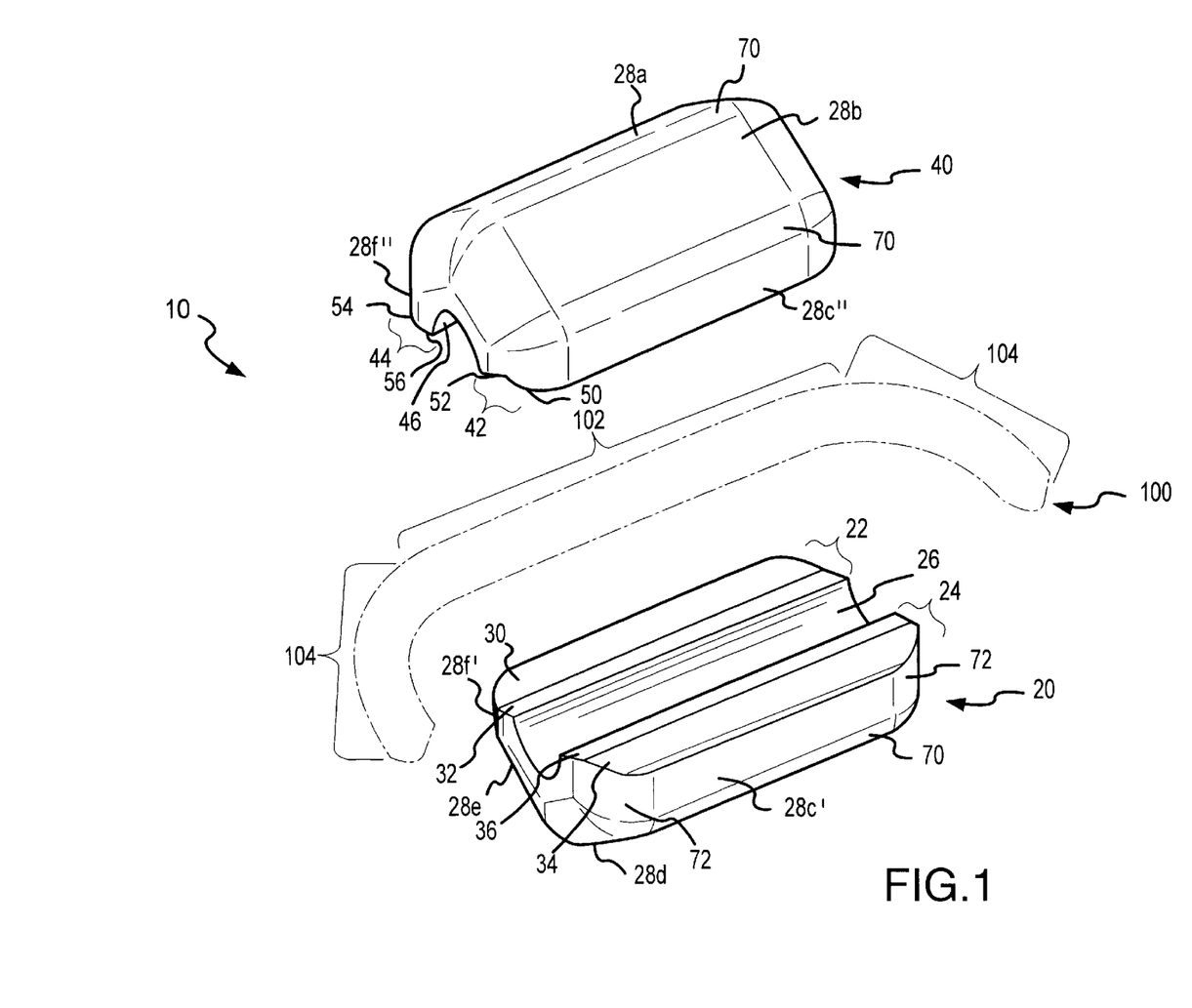
FIG. 1 is an isometric view of one roller embodiment comprising the present invention.

The roller embodiment 10 shown in FIG. 1 comprises a first roller section 20 and second roller section 40 which are configured for ready interconnection with and rolling contact about a wire member 100 comprising an orthodontic device. As will be appreciated, numerous alternative roller embodiments and applications are possible.

In the illustrated roller embodiment 10, the first and second roller sections 20 and 40 are identically configured but reversed in their orientations. More particularly, first roller section 20 and second roller section 40 each include a commonly configured first interface surface 22 (facing up in FIG. 1) and 42 (facing down in FIG. 1), respectively. Similarly, the first roller section 20 and second roller section 40 each include a commonly-configured second interface surface 24 (facing up in FIG. 1) and 44 (facing down in FIG. 1), respectively. As shown, the first and second roller sections 20 and 40 may be opposingly oriented so that the first and second interface surfaces 22 and 24 of the first roller section 20 can be interfit in face-to-face relation with the second and first interface surfaces 44 and 42 of the second roller section 40, respectively.

As further shown in FIG. 1, the first roller section 20 and second roller section 40 each include a groove 26 and 46, respectively, that extends from one end to the other of each given roller section. While each of the illustrated grooves 26 and 46 is of an arcuate configuration (e.g. semicircular in cross-section), other groove configurations may be employed. The grooves 26 and 46 are oriented within first and second roller sections 20 and 40, respectively, so that they collectively define a channel through the roller embodiment 10 upon interconnection of the first and second roller sections 20 and 40. As will be further described, such channel is sized to receive a central section 102 of the wire member 100 of an orthodontic device upon installation.

As shown in FIG. 1, the central section 102 of the wire member 100 may comprise a straight length of wire located between two curved, or bent, sections 104 which, with some types of appliances, may be bent at right angles. In other embodiments, the roller sections 20, 40 may be of a reduced length and/or may define a relatively large channel therethrough (e.g. relative to the diameter of wire member 100), so as to allow for ready interconnection to and rolling engagement with a curved segment of a wire member comprising an orthodontic appliance.

In the latter regard, it should be noted that the invention and described roller embodiment 10 may be employed in connection with a variety of orthodontic devices, including orthodontic appliances having a separate orthodontic treatment function. In particular, roller embodiment 10 may be implemented on a wire member 100 of an orthodontic appliance so that dual functionality is realized. By way of primary example, roller embodiment 10 may be readily interconnected to a trans-palatal wire member 100 of an orthodontic appliance directed to expansion of the palate of the patient, including quad-helix appliances as will be further discussed.

Figure 2A:
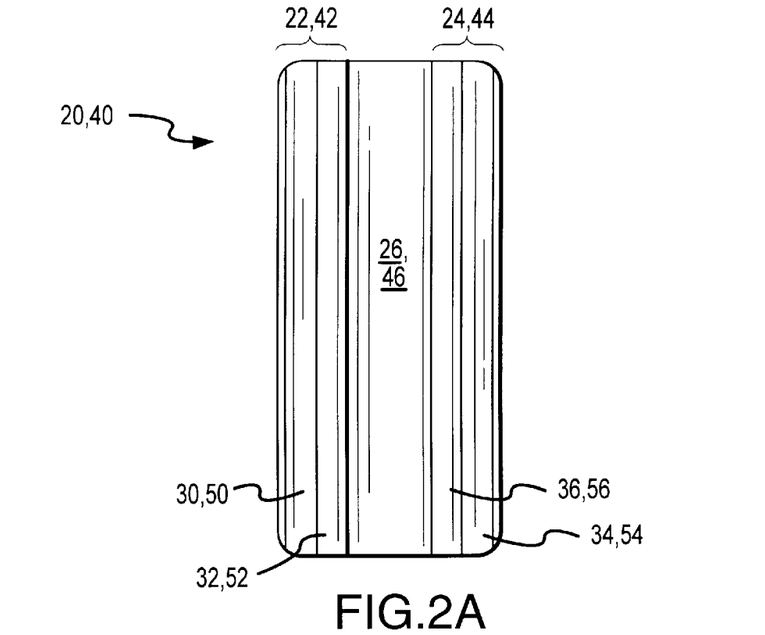
FIGS. 2A–2C illustrate top, end and side views, respectively of roller sections comprising the roller embodiment of FIG. 1.
Figure 2B:
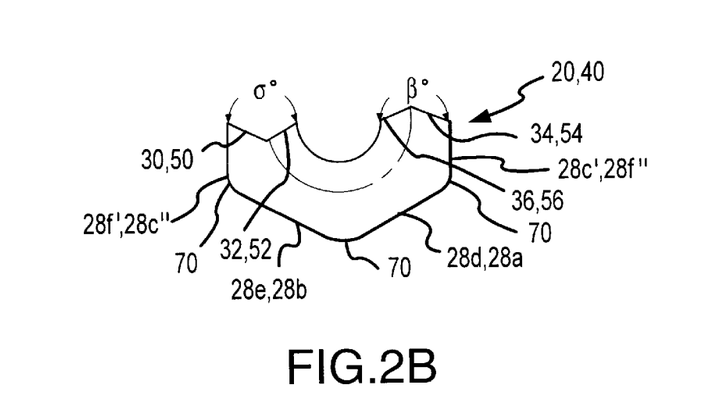
Figure 2C:
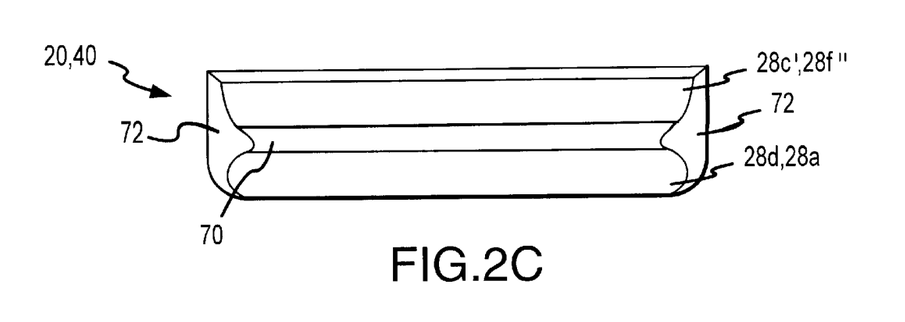

Referring to FIGS. 2A–2C, end, top and side views of the first roller section 20 are illustrated. As will be appreciated, since the first and second roller sections 20 and 40 are identically configured, FIGS. 2A–2C may also apply to the second roller section 40 and therefore reference numerals corresponding with each roller section are provided.

As shown in FIGS. 2A–2C as well as FIG. 1, the first interface surfaces 22 and 42 of the first and second roller sections 20 and 40, respectively, each comprise first and second facets 30, 32 and 50, 52. respectively. Similarly, the second interface surfaces 24 and 44 also comprise first and second facets 34, 36 and 54, 56, respectively. The first and second facets 30, 32 and 50, 52 of the first and second roller sections 20 and 40 adjoin to define concave first interface surfaces 22, 42, respectively. More particularly, the first and second facets, 30, 32 and 50, 52 of each of the first interface surfaces 22 and 42 are flat and adjoin at an open angle σ. Preferably, in such an arrangement, σ<180°, and most preferably 90°<σ<180°. In the illustrated arrangement, σ=150°. Similarly, the second facets 34, 36, and 54, 56 of the first and second roller sections 20 and 40 adjoin to define convex second interface surfaces 24 and 44, respectively. More particularly, the second facets 34, 36 and 54, 56 are flat and adjoin at an open angle β. Preferably, β>180°, and most preferably, 180°<β<270°. In the illustrated embodiment, β=210°. As will be appreciated, σ and β are complimentary angles (i.e. wherein σ°+β°=360°).

With further reference to FIG. 1, it can be seen that the first roller section 20 includes flat outer surfaces 28d, 28e, 28c' and 28f", and second roller section 40 includes flat outer surfaces 28a, 28b, 28c" and 28f'. Whereupon interconnection of the first roller section 20 and second roller section 40, the roller embodiment 10 comprises six outer surfaces 28a–28f defining a hexagonal cross-section. In this regard, it will be appreciated that outer surfaces 28c' and 28f' of the first roller section 20 adjoin with outer surfaces 28c" and 28f" of the second roller section 40 to define sides 28c and 28f of the roller embodiment 10.

It is noted that it maybe preferable for sides 28a–28f to adjoin at sharp edges so as to yield enhanced tactile tongue response. Alternatively, and as illustrated in FIGS. 1–2, all the outer surfaces of the roller embodiment 10 may be configured to present arcuate, smooth transitions between adjacent surface areas. For example, each of the adjacent outer surfaces 28a–28f transition through a smooth radius region 70. Similarly, the outer surfaces at the ends of each roller section 20, 40 of roller embodiment 10 are rounded through transition region 72 toward a center axis of groves 26, 46.

In the illustrated embodiment, grooves 26 and 46 may be sized to define a channel through roller embodiment 10 having a cross-sectional diameter that is slightly greater than the diameter of the central wire section 102 of wire member 100. In this regard, the clearance between the channel of the roller embodiment 10 and the central wire section 102 should be sufficient to allow the roller embodiment 10 to rotate about the central wire section 102 upon contact with the tongue of the patient. For example, regardless of the respective cross-sectional shapes of the central wire section 102 and of the channel of the roller embodiment 10, a minimum difference of at least about 0.010 inches should be provided between the minimum width of the channel and the maximum width of the central wire section 102.

Preferably, grooves 26 and 46 have a constant radius, 180° semicircular cross-sectional configuration and are located such that the grooves 26 and 46 define a channel through the roller embodiment that is circular in cross-section and centered on a central axis extending between the ends of the roller. When both the channel of the roller embodiment 10 and central wire section 102 are circular in cross-section, the ratio between the diameter of the central section 102 and the diameter of the channel should be between about 1/1.1 to 1/2.5. As such, for a wire having a diameter of 0.040 inches, the diameter of the channel of the roller embodiment 10 is preferably between about 0.044 inches to 0.10 inches. In this regard, hygiene has been found to be a consideration and an excessively tight interfit would preclude normal flushing and rinsing of food debris and bacteria from within the channel.

Figure 3A:
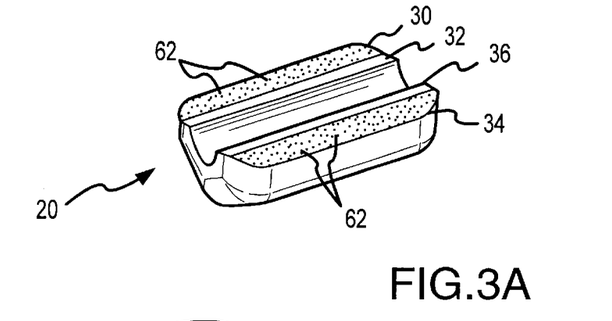
FIGS. 3A–3C illustrate progressive steps in the installation of the roller embodiment of FIG. 1 on an orthodontic appliance.
Figures 3B, 3C:
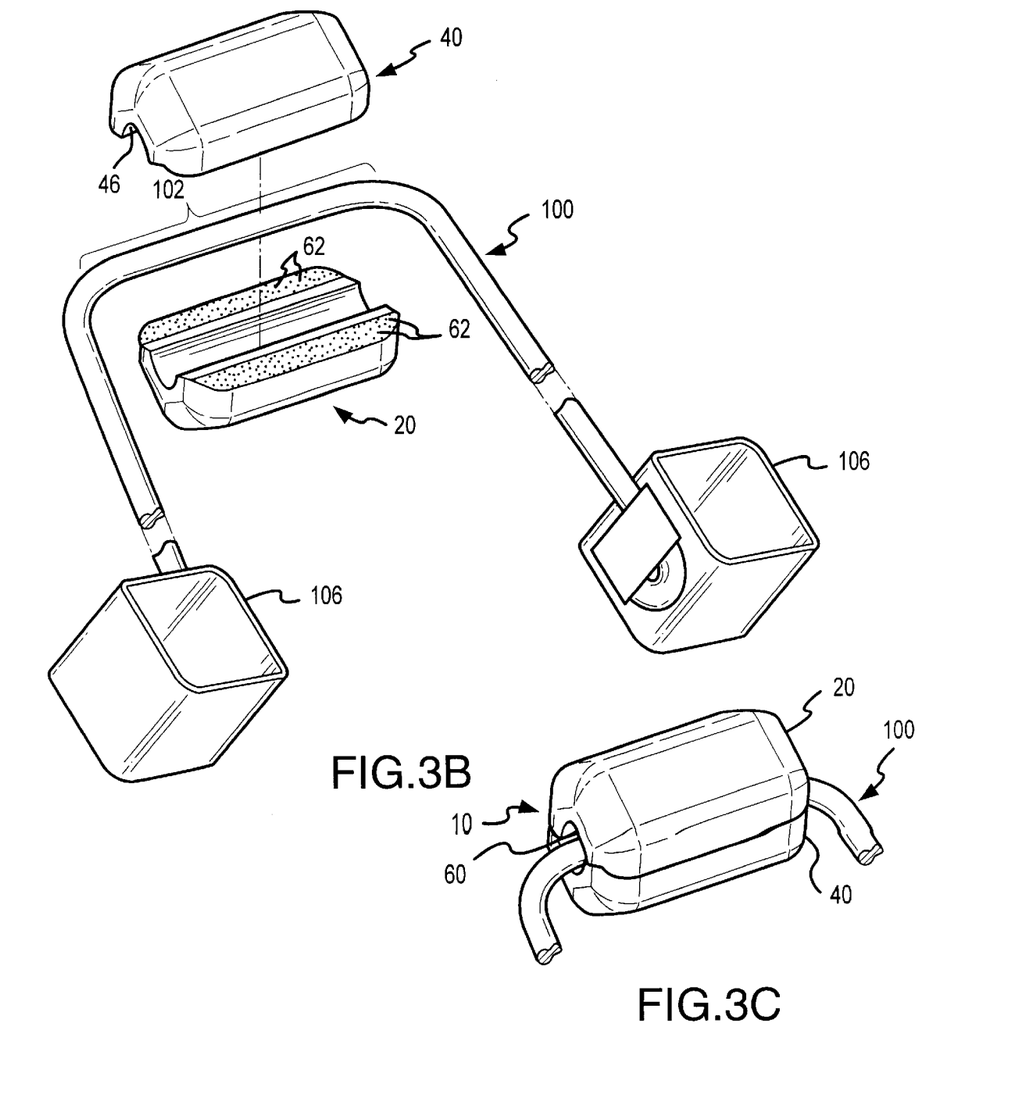

FIGS. 3A–3C will now be referred to for purposes of describing installation of the above-described roller embodiment 10 on an orthodontic device. As shown in FIG. 3A, an adhesive 62 may be selectively applied to the first and second interface surfaces 22, 24 of the first roller section 20. More particularly, it may be preferable to apply adhesive 62 to only the first facet 30 of the first interface region 22 and to the first facet 34 of the second interface surface 24. In this manner, the adhesive 62 is less likely to undesirably migrate into grooves 26, 46 upon interconnection to an orthodontic appliance.

As shown in FIG. 3B, the first roller section 20 may then be positioned adjacent to central section 102 of a wire member 100 comprising an orthodontic device. By way of example, the orthodontic device shown in FIG. 3B is of a custom fabricated type that would serve only to position the roller embodiment 10 in the desired palatable position. Such a device would most likely be attached to the upper first molars. Attachment could be accomplished by means of soldering the wire member 100 to the lingual side of molar bands 106 as illustrated. Alternatively, the wire member 100 could engage the molars via a "fixed removable" means, e.g. employing a horizontal sheath or vertically inserting posts.

As shown in FIG. 3C, upon positioning of the first and second roller sections 20, 40 relative to the wire member 100, the first and second roller sections 20, 40 may be advanced wherein the opposing facets 30, 54, 34, 50, 32, 56 and 36, 52 of first and second roller sections 20 and 40, respectively, are interfit with one another. In this regard, interconnection may be readily established via proper selection of adhesive 62, wherein central wire section 102 is loosely captured in grooves 24, 46.

By way of example, when the first and second roller sections comprise a ceramic material such as polycrystalline alumina, adhesive 62 may comprise a light-activated urethane dimethacrylate system. Alternatively, when the first and second roller sections comprise a plastic material such as polycarbonate, adhesive 62 may comprise bisphenol diglycidol methacrylate. When translucent material, such as poly-crystalline alumina, is utilized to fabricate roller sections 20, 40 (e.g. a material passing between about 20% and about 100% of incident light) adhesive 62 may be light-curable, such as a light-activated urethane dimethacrylate system.

It should be noted that the first and second interface surfaces 22, 24 and 42, 44 of the first and second roller sections 20, 40 may be appropriately prepared before application of adhesive 62 to enhance the bond between the roller sections. For example, when the roller sections 20, 40 comprise a steel or ceramic material, a silane bond coupling agent may be employed. For polycarbonate roller, a compatible adhesive primer may be applied. For acryllic roller sections 20, 40, methyl methacrylate may be used as a primer.

Figure 4A:
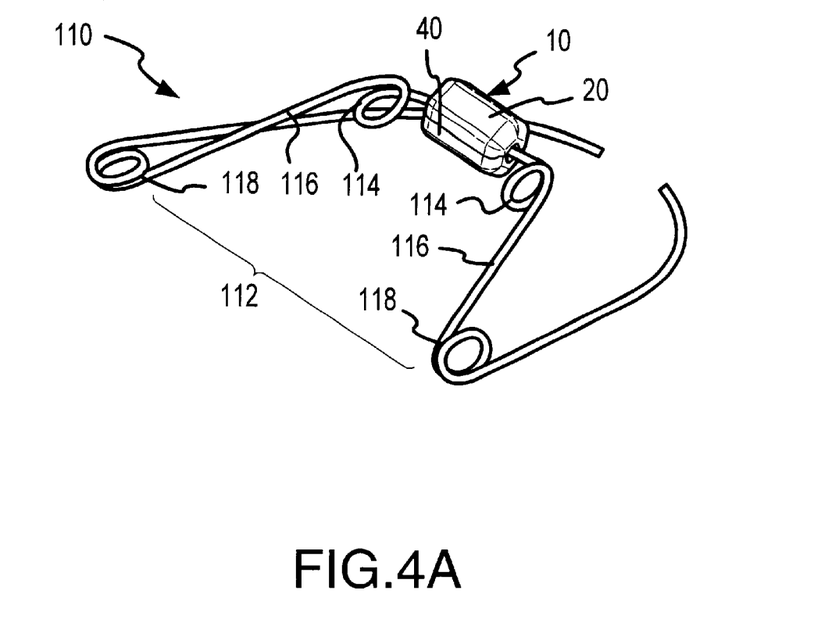
FIGS. 4A and 4B illustrate isometric and top views of an implementation of the roller embodiment of FIG. 1 on a quad-helix type orthodontic appliance.
Figure 4B:
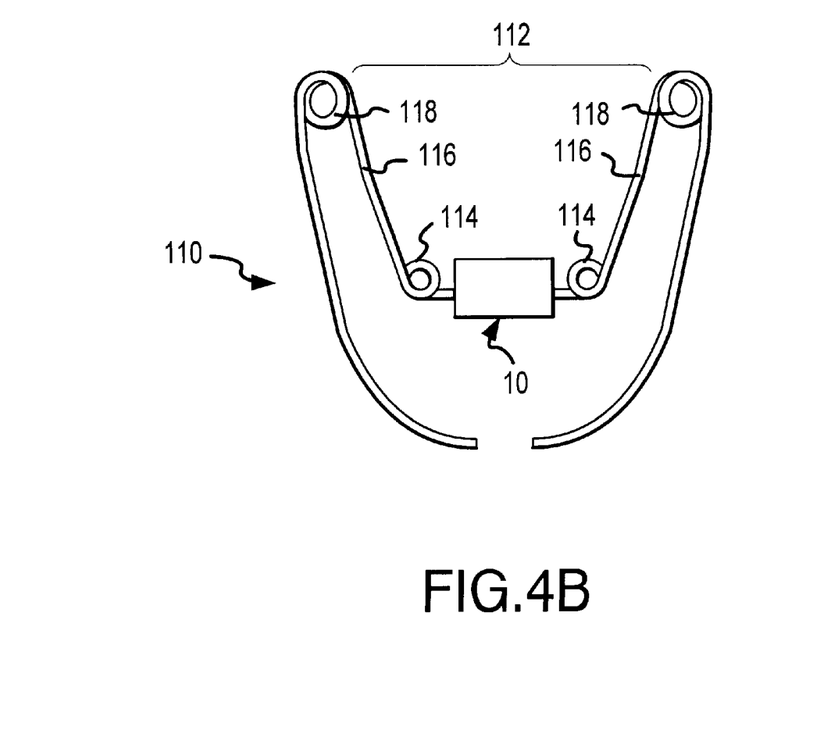

The present invention may be employed on a variety of orthodontic appliances. By way of primary example, the roller embodiment 10 may be readily installed on quad-helix type appliances. Such an installation is shown in FIGS. 4A and 4B. The illustrated quad-helix appliance 110 may be attached to the lingual of the upper first molars. The appliance 110 has a palatal wire section 112 that contains two tightening, round helixes 114 and two anteriorly directed arms 116 that extend around the lingual of the upper teeth. Each anteriorly extending arm 116 has one additional helix 118, to yield a total of four helixes in the appliance, hence the name "quad-helix". The palatal section 112 essentially widens the palate of a patient sagittally. As illustrated, the roller embodiment 10 of the present invention would most commonly be installed between the two palatal helixes 114 of the quad-helix 110. Such a set-up permits routine treatment objectives utilizing the quad-helix (e.g. widening of the palate in one case) and an oral habit breaking objective utilizing the present invention to be undertaken simultaneously. It should be appreciated that the roller embodiment 10 of the present invention may also be installed on an appliance having the sole function of positioning the roller 10 in the patient's palate to achieve an oral habit breaking objective and not serving other treatment objectives as well.

Figure 5A:
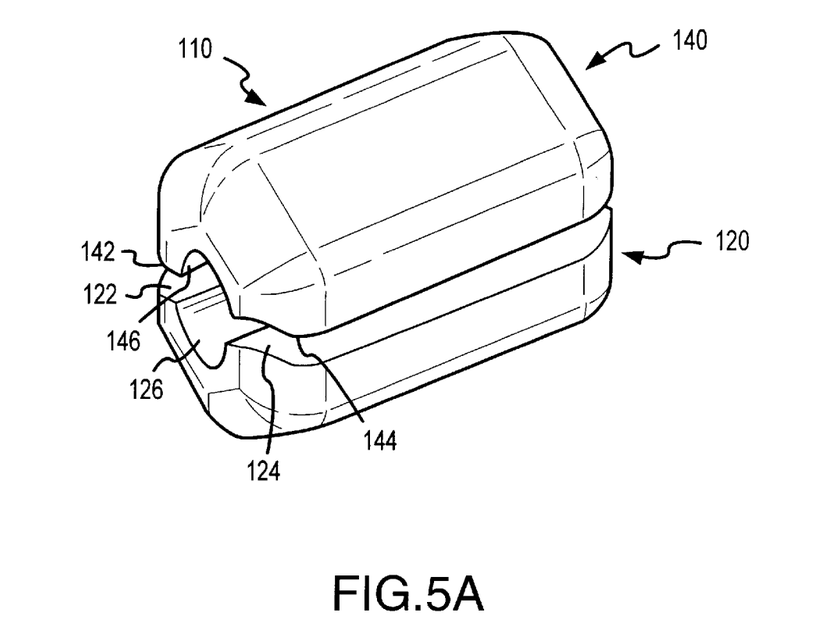
FIGS. 5A and 5B illustrate isometric and end views, respectively of another roller embodiment comprising the present invention.
Figure 5B:
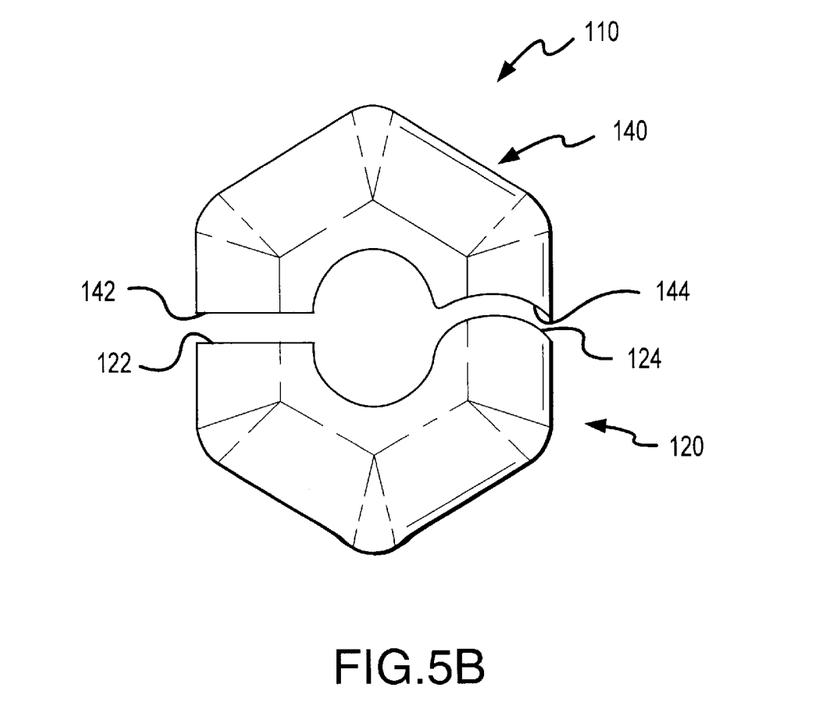

Referring now to FIGS. 5A and 5B, it should be appreciated that a roller in accordance with the present invention need not be comprised of identically configured first and second roller sections. Rather, the first and second roller sections may comprise male and female counterparts configured for ready interconnection with one another to form a roller. FIGS. 5A and 5B illustrate an example of a such a roller 210 having a male first roller section 220 and a female second roller section 240. The male first roller section 220 includes a flat first interface surface 222 and a convex second interface surface 224. The female second roller section includes a flat first interface surface 242 and a concave second interface surface 244. When the roller sections 220, 240 are interconnected about a wire member, the flat first interface surface 222 of the first roller section 220 interfaces with the flat first interface surface 242 of the second roller section 240. Likewise, the convex second interface surface 224 of the first roller section 220 interfaces with the concave second interface surface 244 of the second roller section 240.

Figure 6A:
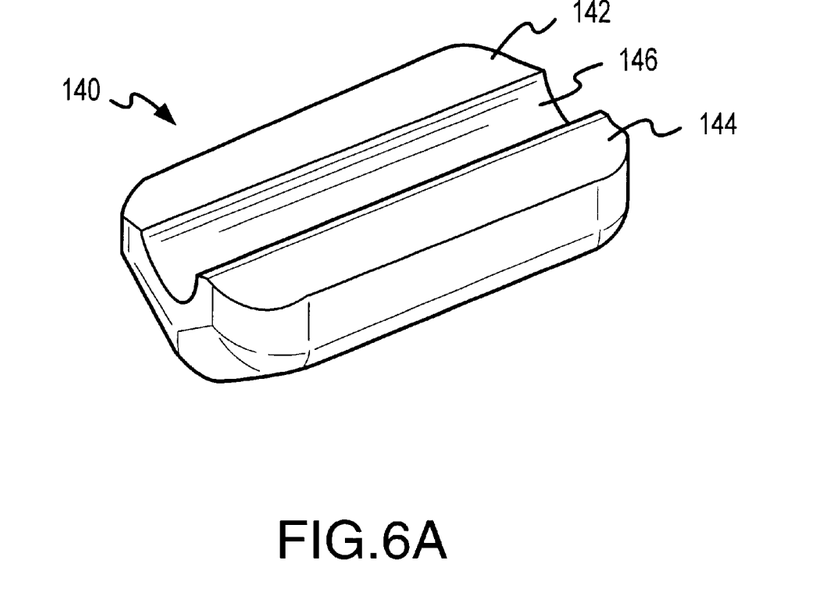
FIGS. 6A and 6B illustrate isometric and end views, respectively of a roller section of the roller embodiment of FIGS. 5A and 5B.
Figure 6B:
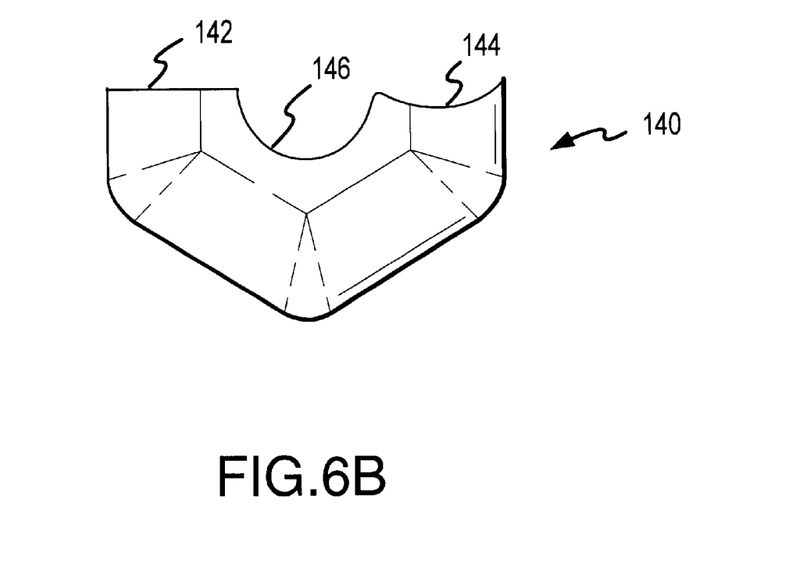

In FIGS. 6A and 6B, isometric and end views of the second roller section 240 are illustrated with its first and second interface surfaces 242, 244 shown facing up. As can be seen, the second roller section 240 includes a groove 246 extending from one end to the other of the second roller section 240. As can be seen in FIGS. 5A and 5B, the first roller section 220 includes a corresponding groove 226 extending from end to the other of the first roller section 220. As with the previously described roller embodiment 10, the grooves 226, 246 may be configured differently than the arcuate configuration shown, and, when the first and second roller sections 220, 240 are interconnected, the grooves 226, 246 collectively define a channel through the roller 210 that is sized to receive a central section of a wire member of an orthodontic device.

Figure 7:
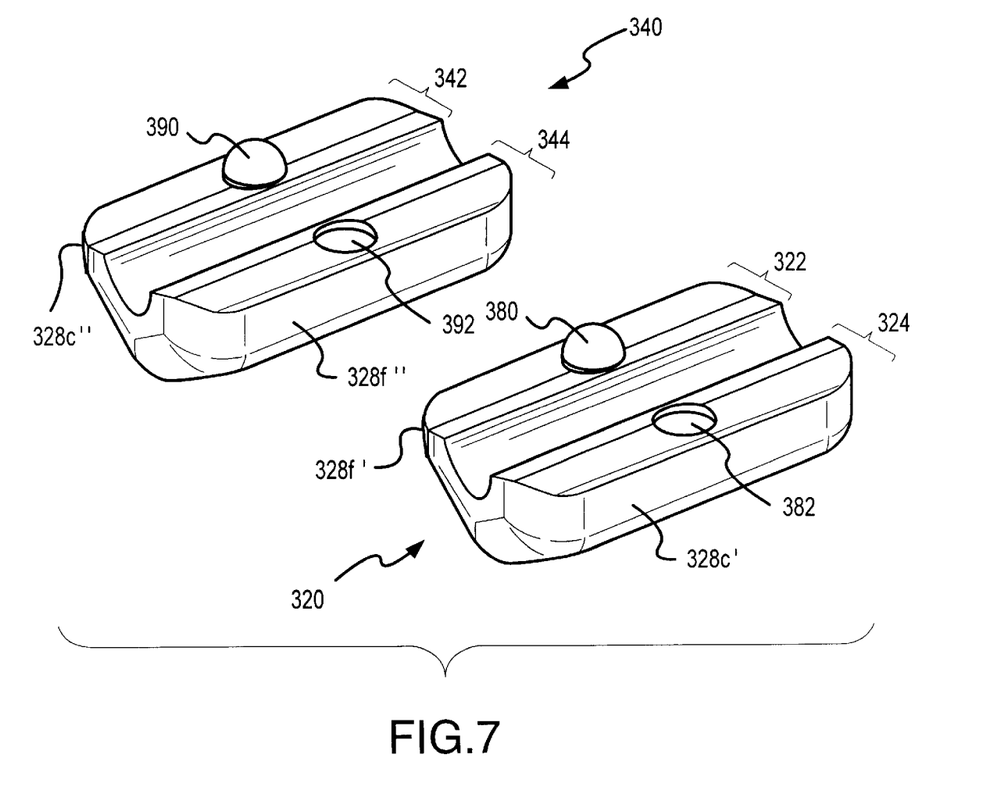
FIG. 7 illustrates an isometric view of identically configured roller sections of a further roller embodiment comprising the present invention wherein the roller sections include lateral registration surfaces.
Figure 8:
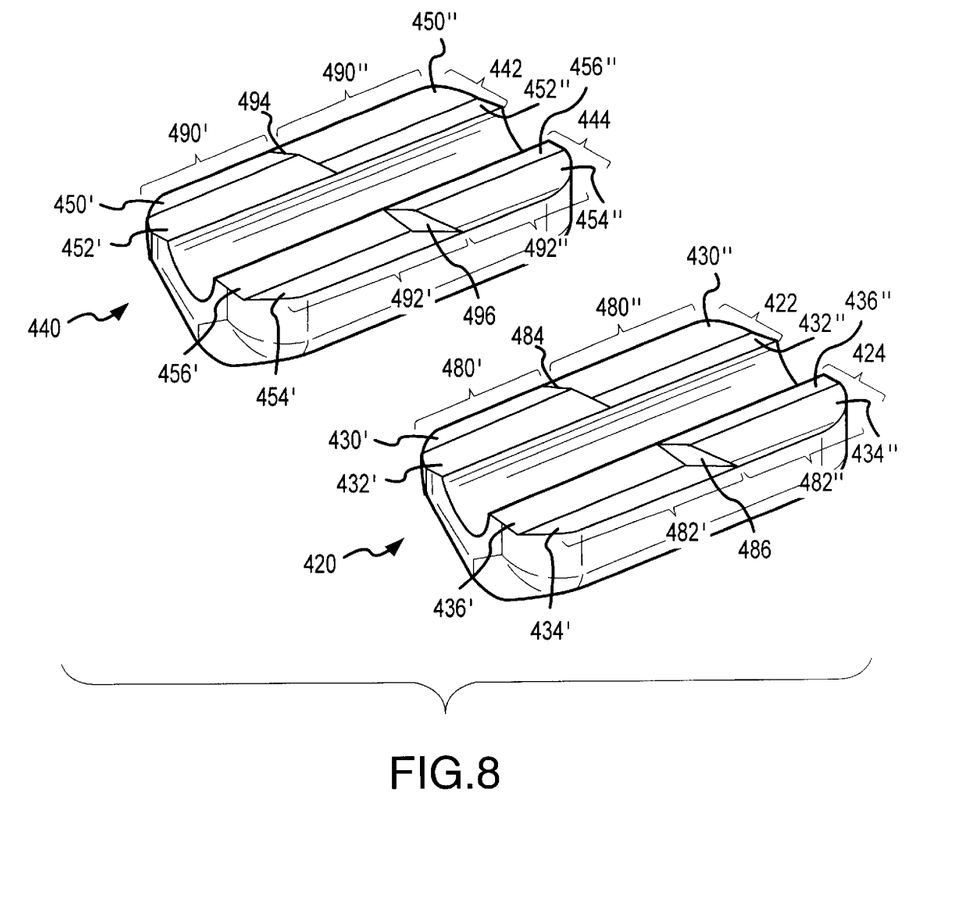
FIG. 8 illustrates an isometric view of identically configured roller sections of an additional roller embodiment comprising the present invention wherein the roller sections include lateral registration surfaces.

Referring now to FIGS. 7 and 8, the roller sections comprising a roller in accordance with the present invention may each include one or more registration surfaces for facilitating lateral alignment of the roller sections during interconnection.

For example, FIG. 7 shows identically configured first and second roller sections 320, 340 wherein the first roller section 320 includes first and second registration surfaces 380, 382 and the second roller section 340 includes similarly configured first and second registration surfaces 390, 392. The first registration surface 380, 390 of each roller section 320, 340 may be configured in the shape of a convex hemisphere extending from a first interface surface 322, 342 of the roller sections 320, 340. The second registration surface 382, 392 may be configured as a concave hemisphere extending into a second interface surface 324, 344 of the roller sections 320, 340. The first registration surface 380 of the first roller section 320 is appropriately sized and located to engage with the second registration surface 392 of the second roller section 340 as the first interface surface 322 of the first roller section 320 and the second interface surface 344 of the second roller section 340 are advanced towards one another when interconnecting the roller sections 320, 340. Likewise, the first registration surface 390 of the second roller section 340 is appropriately sized and located to engage with the second registration surface 382 of the first roller section 320 as the first interface surface 342 of the second roller section 340 and the second interface surface 324 of the first roller section 340 are advanced towards one another when interconnecting the roller sections 320, 340. It will be appreciated that with the respective registration surfaces 380, 392 and 390, 382 thus engaged, lateral movement of the first and second roller sections 320 and 340 will be restricted in two dimensions. It will also be appreciated that with the registration surfaces 380, 382 and 390, 392 located as shown in FIG. 7, when the respective registration surfaces 380, 392 and 390, 382 are engaged, the ends of the first and second roller sections 320 and 340 will be substantially aligned and outer surfaces 328c' and 328f' of the first roller section 320 will adjoin with outer surfaces 328c" and 328f' of the second roller section 340 to combinatively define sides that are substantially continuous and smooth.

FIG. 8 shows another example of identically configured first and second roller sections 420, 440 having registration surfaces for facilitating lateral alignment of the roller sections 420, 440 during interconnection. The first and second roller sections 420 and 440 each include first and second interface surfaces 422, 424 and 442, 444, respectively. The first interface surface 422 of the first roller section 420 comprises a partially convex portion 480' defined by a pair of adjoining facets 430', 432' and a partially concave portion 480" defined by a pair of adjoining facets 430", 432". A first registration surface 484 of the first roller section 420 is defined where the partially convex and partially concave portions 480' and 480" adjoin. The second interface surface 424 of the first roller section 420 comprises a partially concave portion 482' defined by a pair of adjoining facets 434', 436' and a partially convex portion 482" defined by a pair of adjoining facets 434", 436". A second registration surface 486 of the first roller section 420 is defined where the partially concave and partially convex portions 482' and 482" adjoin. The first interface surface 442 of the second roller section 440 comprises a partially convex portion 490' defined by a pair of adjoining facets 450', 452' and a partially concave portion 490" defined by a pair of adjoining facets 450", 452". A first registration surface 494 of the second roller section 440 is defined where the partially convex and partially concave portions 490' and 490" adjoin. The second interface surface 444 of the second roller section 440 comprises a partially concave portion 492' defined by a pair of adjoining facets 454', 456' and a partially convex portion 492" defined by a pair of adjoining facets 454", 456". A second registration surface 494 of the second roller section 440 is defined where the partially concave and partially convex portions 492' and 492" adjoin. When the first and second roller sections 420, 440 are interconnected by interfacing the first interface surface 422 of the first roller section 420 with the second interface surface 444 of the second roller section 440 and the second interface surface 424 of the first roller section 420 with the first interface surface 442 of the second roller section 440, the first and second roller sections 420 and 440 may also be moved laterally relative to one another to engage the first registration surface 484 of the first roller section 420 with the second registration surface 496 of the second roller section 440 and the second registration surface 486 of the first roller section 420 with the first registration surface 494 of the second roller section 440. It will be appreciated that the first registration surface 484 of the first roller section 420 and the second registration surface 496 of the second roller section 440 comprise a first pair of opposing surfaces that restrict movement of the roller sections 420, 440 relative to one another in one dimension. Likewise, the second registration surface 486 of the first roller section 420 and the first registration surface 494 of the second roller section 440 comprise another pair of opposing surfaces that restrict movement of the roller sections 420, 440 relative to one another in one dimension. It will also be appreciated that with the respective registration surfaces 484, 496 and 486, 494 positioned as shown in FIG. 8, the ends of the first and second roller sections 420, 440 will be in substantial lateral alignment when the respective pairs of registration surfaces 484, 496 and 486, 494 are engaged.

Referring again to FIGS. 3A–3C, it will be appreciated that when the first and second roller sections 20, 40 include lateral registration surfaces (not shown in FIGS. 3A–3C), such as, for example, registration surfaces as shown in FIGS. 7 and 8, installation of the roller 10 on an orthodontic device may include additional procedures. For example, if the roller sections are configured as shown in FIG. 7, as the roller sections 20, 40 are advanced towards one another to loosely capture wire member 100, the roller sections 20, 40 may be moved laterally relative to one another in two dimensions until respective registration surfaces of the roller sections are engaged with one another. As another example, if the roller sections are configured as shown in FIG. 8, the roller sections 20, 40 may be advanced towards one another until they are interconnected in an overlapping fashion (e.g. with the second roller section 40 offset to the left relative to the first roller section 20) loosely capturing wire member 100. The roller sections 20, 40 may then be moved laterally in one dimension (e.g. the second roller section 40 may be shifted to the right relative to the first roller section 40) to engage the respective registration surfaces of the roller sections 20, 40 with one another.

It should be appreciated that registration surfaces for facilitating lateral alignment of the roller sections, such as depicted in FIGS. 7 and 8, may serve several functions. For example, the lateral registration surfaces facilitate alignment of the ends of the roller sections thereby limiting the likelihood that a possibly sharp edge or shelf projects from each end of the roller. The lateral registration surfaces also provide time savings during the installation process, particularly when the roller is installed on an appliance previously positioned in a patient's mouth and light for curing the adhesive and space are limited.

Numerous additional modifications, extensions and embodiments of the present invention will be apparent to one skilled in the art and are intended to be within the scope of the present invention as defined by the claims that follow.

What is claimed is:

1. A device for oral use comprising:
   a wire member formed for lingual positioning in a patient's mouth;
   a first roller section having an interface surface; and
   a second roller section having an interface surface, said first and second roller sections being interconnectable in opposing, face-to-face relation to define a roller with a channel between said interface surfaces of said first and second roller sections, said channel being sized to selectively receive a portion of said wire member therethrough upon interconnection of said first and second roller sections, wherein said roller is rotatable about said wire member.

2. A device as recited in claim 1, wherein said first roller section comprises at least one convex surface and said second roller section comprises at least one concave surface, said convex and concave surfaces being correspondingly shaped, and wherein said concave surface conformally receives said convex surface upon interconnection of said first and second roller sections.

3. A device as recited claim 2, wherein said first roller section comprises a concave surface and said second roller section comprises a convex surface, said concave surface of said first roller section and said convex surface of said second roller section being correspondingly shaped, wherein said concave surface of said first roller section conformally receives said convex surface of said second roller section upon interconnection of said first and second roller sections.

4. A device as recited in claim 1, wherein at least one of said interface surfaces comprises a groove extending across the entirety of such interface surface.

5. A device as recited in claim 1, wherein each of said interface surfaces comprises a groove extending across the entirety of such interface surface, and wherein said grooves are correspondingly oriented to define said channel upon interconnection of said first and second roller sections.

6. A device as recited in claim 1, wherein said interface surfaces of said first and second roller sections each comprise first and second interface surfaces on opposing sides of a groove defined across each respective interface surface, wherein said grooves define said channel upon interconnection of said first and second roller sections, and wherein said first interface surface of said first roller section interfaces with said second interface surface of said second roller section and said second interface surface of said first roller section interfaces with said first interface surface of said second roller section upon interconnection of said first and second roller sections.

7. A device as recited in claim 6, wherein said first interface surfaces of said first and second roller sections are convexly shaped, and wherein said second interface surfaces of said first and second roller sections are concavely shaped.

8. A device as recited in claim 6, wherein each of said first and second roller sections comprise contoured outer surfaces and wherein said contoured outer surfaces of said first and second roller sections are configured so that said roller is of an elongated configuration upon interconnection of said first and second roller sections.

9. A device as recited in claim 8, wherein said contoured outer surfaces of said first and second roller sections are configured so that said roller is of a cylindrical configuration upon interconnection of said first and second roller sections.

10. A device as recited in claim 9, wherein said contoured outer surfaces of said first and second roller sections are configured so that said roller is of hexagonal cross-sectional configuration.

11. A device as recited in claim 9, wherein said outer contoured surfaces of said first and second roller sections are configured so that said roller has outer tactile contouring comprising at least one of: troughs, ribs, annular rings, pockets and bumps.

12. A device as recited in claim 6, wherein said first interface surfaces of said first and second roller sections each comprise first and second facets which adjoin at an open first angle of less than 180 degrees, and wherein said second interface surfaces of said first and second roller sections each comprise first and second facets that adjoin at an open second angle greater than 180 degrees.

13. A device as recited in claim 12, wherein said first and second open angles are complimentary.

14. A device as recited in claim 1, wherein said first roller section and said second roller section comprise a ceramic material.

15. A device as recited in claim 1, wherein said first roller section and second roller section comprise a translucent material selected from a group consisting of: a ceramic material, a plastic material, and a composite material.

16. A device for oral use comprising:
a wire member formed for lingual positioning in a patient's mouth;
a first roller section; and
a second roller section, said first and second roller sections being interconnectable in opposing, face-to-face relation to define a roller with a channel therebetween, said channel being sized to selectively receive a portion of said wire member therethrough upon interconnection of said first and second roller sections, and wherein said first roller section includes at least one registration surface and said second roller section includes at least one registration surface, said registration surfaces of said first and second roller sections being engagable with one another upon interconnection of said first and second roller sections to establish a desired aligned position of said first roller section relative to said second roller section.

17. A device as recited in claim 16, wherein said registration surfaces of said first and second roller sections are engagable with one another to dispose respective ends of said first and second roller sections in substantial alignment.

18. A device as recited in claim 16, wherein said first roller section includes first and second registration surfaces and said second roller section includes first and second registration surfaces, wherein said first registration surface of said first roller section is engagable with said second registration surface of said second roller section and said second registration surface of said first roller section is engagable with said first registration surface of said second roller section upon interconnection of said first and second roller sections, and wherein upon interconnection of said first and second roller sections said first and second registration surfaces of said first and second roller sections restrict relative movement of said first and second roller sections in at least one dimension.

19. A device as recited in claim 18, wherein upon interconnection of said first and second roller sections said first and second registration surfaces of said first and second roller sections restrict relative movement of said firs second roller sections in two dimensions.

20. A device as recited in claim 16, wherein upon interconnection of said first and second roller sections said at least one registration surface of said first roller section and said at least one registration surface of said second roller section restrict relative movement of said first and second roller sections in at least one dimension.

21. A device as recited in claim 20, wherein said at least one registration surface of said first roller section and said at least one registration surface of said second roller section restrict relative movement of said first and second roller sections in two dimensions and are configured so that said at least one registration surface of said first roller section matingly receives said at least one registration surface of said second roller section upon interconnection of said first and second roller sections.

22. A device as recited in claim 21, wherein said at least one registration surface of said first roller section is of a convex, hemispherical configuration and said at one registration surface of said second roller section is of a concave, hemispherical configuration.

23. A device for oral use comprising:
an arcuate-shaped wire member having a central section disposed between opposing curved sections, said wire member being formed for lingual positioning in a patient's mouth wherein the central section is positionable in a patient's palate; and
a first roller having a channel therethrough for selective installation on and rollable positioning about said central section of said wire member free from sliding passage over said opposing curved sections of said wire member, said first roller including first and second sections selectively interconnectable upon installation to define said channel therebetween.

24. A device as recited in claim 23 having a minimum difference between a minimum width of said channel and a maximum width of said central section of said wire member of at least about 0.010 inches.

25. A device as recited in claim 19, said wire member having a first diameter and said channel having a second diameter, wherein the ratio of said second diameter to said first diameter is between about 1/1.1 and 1/2.5.

26. A device as recited in claim 23, wherein said wire member is part of an orthodontic appliance having an orthodontic functionality separate from a functionality of said oral habit retraining device.

27. A device as recited in claim 26, wherein said orthodontic appliance is selected from a group consisting of: a quad-helix orthodontic appliance, a rapid palatal expander appliance, a bi-helix orthodontic appliance, and a multi-functional palatal appliance.

28. A device as recited in claim 23, wherein said roller is free to move laterally from side to side along said central section of said member, and wherein said central section of said wire member is a first length which is greater than a second length of said roller by at least about 0.020 inches.

29. A device as recited in claim 23, further comprising:
a second roller having a channel therethrough for selective installation on and rollable positioning about said central section of said wire member free from sliding passage over said opposing curved sections of said wire member.

30. A method for installing a device for oral use, comprising:
applying an adhesive on at least one of an interface surface of a first roller section and an interface surface of a second roller section;
positioning said first roller section on one side of a central section of a wire member positionable within the vault of the palate of a patient, wherein said interface surface of said first roller section faces said wire member;
positioning a second roller section on an opposing side of said central section of said wire member, wherein said interface surface of said second roller section faces said wire member;
contacting said first roller section and said second roller section, wherein said first and second roller sections are adhesively interconnected with said adhesive to define a roller having a channel therethrough, and wherein said central section of said wire member is loosely captured between said first and second roller sections within said channel.

31. The method of claim 30, said applying step including:
restricting the application of said adhesive to outer facets of said interface surface of said first roller section, said outer facets being spaced from said channel upon interconnection of said first and second roller sections.

32. A method as recited in claim 30, wherein said first and second roller sections comprise a ceramic material, and wherein said adhesive comprises a light-activated urethane dimethacrylate adhesive system.

33. A method as recited in claim 30, further comprising:
fabricating an orthodontic appliance comprising said wire member, wherein said fabricating step is completed prior to said applying, positioning and contacting steps.

34. A method as recited in claim 33, wherein said positioning and contacting steps are completed with said wire member being in an installed position within a patient's mouth.

35. A method as recited in claim 33 further comprising:
utilizing said roller for treatment of an undesired oral habit simultaneously with utilization of said orthodontic appliance to achieve an orthodontic treatment objective separate from said oral habit retraining functionality.

36. A method as recited in claim 30, further comprising:
engaging at least one registration surface of said first roller section with at least one registration surface of said second roller section to establish a lateral position of said first roller section relative to said second roller section.

37. A method as recited in claim 36, wherein, in said step of engaging, a lateral position of said first roller section relative to said second roller section is established wherein respective ends of said first and second roller sections are in substantial alignment.

38. A method for installing a device for oral use in a patient's mouth, comprising:
applying an adhesive on at least one of an interface surface of a first roller section;
positioning said first roller section on one side of a wire member lingually positionable within the mouth of a patient, wherein said interface surface of said first roller section faces said wire member;
positioning a second roller section on an opposing side of said wire member, wherein an interface surface of said second roller section faces said wire member; and
engaging at least one registration surface of said first roller section with at least one registration surface of said second roller section to establish a lateral position of said first roller section relative to said second roller section, wherein said first and second roller sections are adhesively interconnected with said adhesive to define a roller having a channel therethrough.

39. A method as recited in claim 38, further comprising:
restricting relative lateral movement of said first and second roller sections in at least one dimension by subcontact interface between said at least one registration surface of said first roller section and said at least one registration surface of said second roller section.

40. A method as recited in claim 39, wherein said restricting step provides for restriction of relative lateral movement of said first and second roller sections in two dimensions.

41. A method as recited in claim 38, wherein said first and second roller sections comprise a material selected from a group consisting of: a ceramic material, a plastic material, and a composite material.

* * * * *

UNITED STATES PATENT AND TRADEMARK OFFICE
CERTIFICATE OF CORRECTION

PATENT NO.   : 6,082,996
DATED        : July 4, 2000
INVENTOR(S)  : HASKELL

It is certified that error appears in the above-identified patent and that said Letters Patent are hereby corrected as shown below:

At the title page, line [56], FOREIGN PATENT DOCUMENTS, please delete "818242" and insert therefor --818243--.
At Column 7, line 57, please delete "28f'" and insert therefor --28f'--.
At Column 10, line 60, please delete "328f'" and insert therefor --328f'--.
At Column 14, line 18, please delete "firs" and insert therefor --first and--.

Signed and Sealed this

Tenth Day of April, 2001

Attest:

NICHOLAS P. GODICI

Attesting Officer            Acting Director of the United States Patent and Trademark Office